United States Patent [19]
Pierdet et al.

[11] 3,975,413

[45] Aug. 17, 1976

[54] NOVEL HAPTENES AND ANTIGENS

[76] Inventors: Andre Pierdet, 7, rue Pierre Feuillere, 93130 Noisy-le-Sec; Daniel Coussediere, 116, rue Ambroise Croizat, 94800 Villejuif, both of France

[22] Filed: July 2, 1975

[21] Appl. No.: 592,619

[30] Foreign Application Priority Data
July 4, 1974 France .............................. 74.23281

[52] U.S. Cl. ....................... 260/397.1; 260/397.45; 424/238; 260/112 R
[51] Int. Cl.² .................................. C07J 9/00
[58] Field of Search .................. 260/397.1; 424/238

[56] References Cited
OTHER PUBLICATIONS
Chemical Abstracts, (1974), vol. 81, Paragraph 61939g.

*Primary Examiner*—Elbert L. Roberts

[57] ABSTRACT

Novel haptenes of the formula

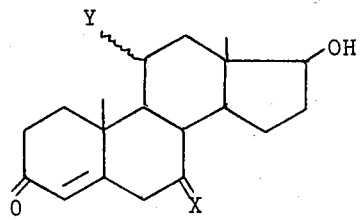

I wherein X is

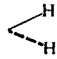

when Y is

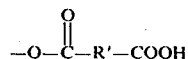

in the α- or β-position and R' is selected from the group of p-phenylene and —(CH$_2$)$_a$—and a is a whole number from 1 to 18 with the proviso that *a* is other than 2 when Y is in the α-position and when Y is hydrogen, X is selected from the group consisting of

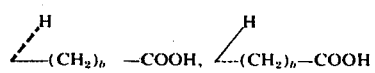

and =N—O—(CH$_2$)$_c$—COOH, *b* is a whole number from 1 to 18 and *c* is a whole number from 1 to 12 useful for the preparation of antigens formed therefrom.

10 Claims, No Drawings

NOVEL HAPTENES AND ANTIGENS

STATE OF THE ART

Steroids [Vol. 21 (5), 1973, p. 723–33] describes 17-oxo-steroids with a double bond in 5(6)-position while the steroids of formula I have a double bond in the 4(5)-position and a 17-hydroxy.

OBJECTS OF THE INVENTION

It is an object of the invention to provide the novel haptenes of formula I.

It is another object of the invention to provide a novel method of producing the haptenes of formula I.

It is a further object of the invention to provide a novel process for preparing antigens and to the novel antigens produced thereby.

These and other objects and advantages of the invention will become obvious from the following detailed description.

THE INVENTION

The novel haptenes of the invention have the formula

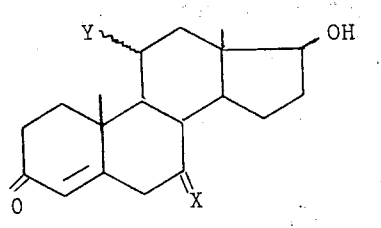

wherein X is

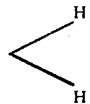

when Y is

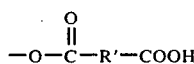

in the α- or β-position and R' is selected from the group of p-phenylene and —$(CH_2)_a$— and $a$ is a whole number from 1 to 18 with the proviso that $a$ is other than 2 when Y is in the α-position and when Y is hydrogen, X is selected from the group consisting of

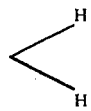

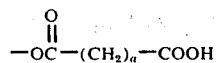

and =N—O—$(CH_2)_c$—COOH, $b$ is a whole number from 1 to 18 and $c$ is a whole number from 1 to 12.

Among the preferred compounds of formula I are those wherein —$(CH_2)_a$—COOH and —$(CH_2)_b$—COOH are the same or different and are derived from an alkanoic acid of 3 to 12 carbon atoms such as propionic acid, butyric acid, pentylic acid, decylic, undecylic or dodecylic acid and —$(CH_2)_c$—COOH is preferably derived from an aliphatic carboxylic acid of 2 to 5 carbon atoms such as acetic acid, propionic acid, butyric acid or pentylic acid.

Notable among the compounds of formula I are those where X is

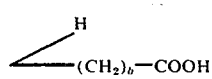

and Y is $$-O\overset{O}{\overset{\|}{C}}-(CH_2)_a-COOH$$

in the α- or 6β-position with the proviso that $a$ is not 2 when Y is in the α-position or Y is

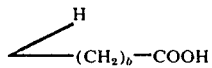

in the α- or β-position and those where Y is hydrogen and X is

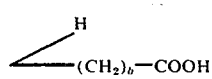

or

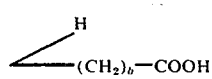

or =NO—$(CH_2)_c$—COOH.

Especially preferred individual compounds of formula I are 11β-hemisuccinoyloxy-Δ⁴-androstene-17β-ol-3-one, 11α- and 11β-hemiterephthaloyloxy-Δ⁴-androstene -17β-ol-3-one, 7α-and 7β-(ω-carboxydecyl)-Δ⁴-androstene-17β-ol-3-one and 7-carboxymethoxyimino-Δ⁴-androstene-17β-ol-3-one.

The novel process of the invention for the production of compounds of formula I wherein X is

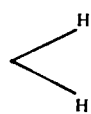

and Y is

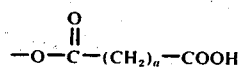

in the α- or β-position wherein a is other than 2 when Y is in the α-position comprises reacting a compound of the formula

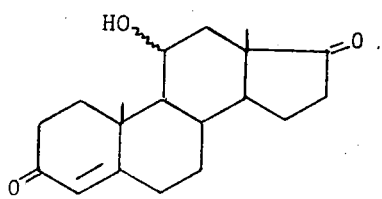
II wherein the hydroxy is in the α- or β-position with an anhydride of the formula

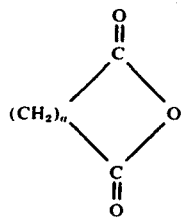
III to obtain a compound of the formula

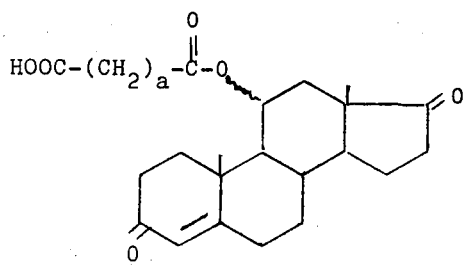
IV and reacting the latter with a reducing agent to obtain corresponding 17β-hydroxy compound of formula I.

The esterification of the compound of formula II is preferaby effected in chloroform in the presence of triethylamine or in pyridine in the presence of dimethylaminopyridine. The reducing agent is preferably a mixed hydride such as lithium borohydride or most preferably sodium borohydride.

The process of the invention to produce a compound of formula I wherein X is

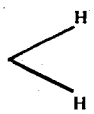

and Y is

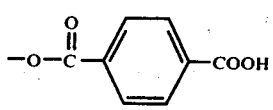

in the α- or β-position comprises reacting a compound of the formula

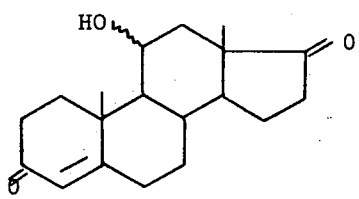
V wherein the 11-OH is in the α- or β-position with a p-carbalkoxybenzoic acid anhydride of the formula Alk$_1$-O-C(=O)-C$_6$H$_4$-C(=O)-O-C(=O)-C$_6$H$_4$-C(=O)-O-Alk$_1$
VI wherein Alk$_1$ is alkyl of 1 to 6 carbon atoms to obtain a compound of the formula

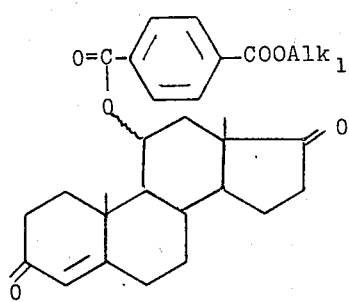

VII which is then reacted with an alkyl orthoformate of the formula

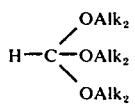

VIII wherein Alk₂ is alkyl of 1 to 6 carbon atoms to obtain a compound of the formula

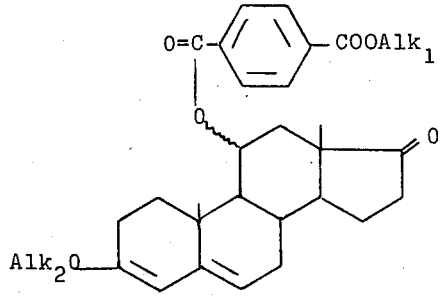

IX subjecting the latter to reduction to obtain a compound of the formula

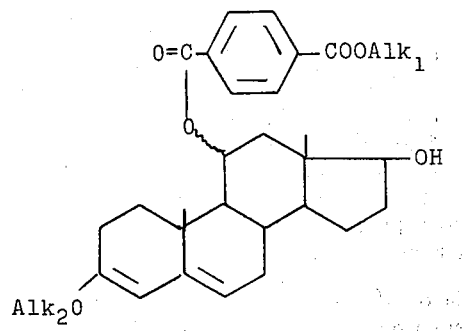

X and reacting the latter with a saponification agent and then an acid hydrolysis agent or reversal of the two steps to obtain the desired compound of formula I.

The p-carbalkoxybenzoic acid anhydride is preferably p-carboxymethylbenzoic acid anhydride or p-carboxyethylbenzoic acid anhydride. The alkyl orthoformate is preferably the methyl, ethyl or propyl orthoformate and the reaction is preferably effected in dioxane in the presence of p-toluene sulfonic acid. The reducing agent is preferably sodium or lithium borohydride.

The saponification agent is preferably an alkaline base such as alkali metal hydroxide like sodium or potassium hydroxide; alkali metal amides such as sodium amide; alkali metal alcoholates such as potassium tert.-butylate; alkali metal acetylides such as lithium acetylide and the reaction is preferably effected in a lower alkanol such as methanol or ethanol or isopropanol. The acid hydrolysis is preferably effected with hydrochloric acid, sulfuric acid, acetic acid, citric acid or p-toluene sulfonic acid and the reaction is preferably effected in one or more solvents such as a lower alkanol like methanol, ethanol or isopropanol.

The starting compounds of formulae II and V may be prepared by the process described in U.S. Pat. Nos. 2,656,370 and 3,072.684.

The process of the invention to produce compounds of formula I wherein Y is hydrogen and X is

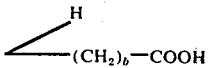

or

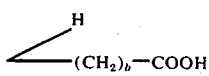

comprises reacting a compound of the formula

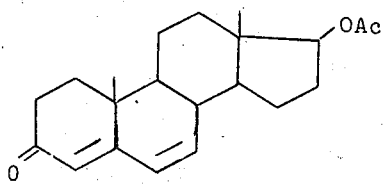

XI wherein Ac is the acyl of an organic carboxylic acid of 1 to 18 carbon atoms with a compound of the formula

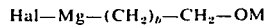 XII wherein Hal is a halogen, b is a whole number of 1 to 18 and OM is a blocked hydroxyl in the form of an ether to obtain a mixture of 7α- and 7β- isomers of the formula

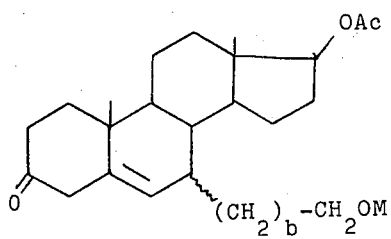 XIIIa and

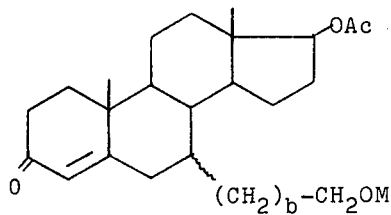 XIIIb reacting the latter with an acid agent to cleave the ethers and form a mixture of 7α- and 7β-isomers of the formula

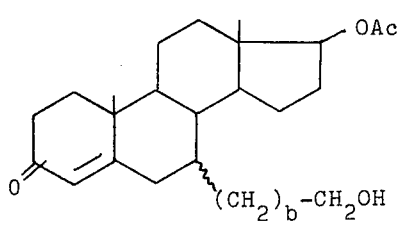 XIV reacting the latter with an oxidation agent to obtain a mixture of 7α- and 7β-isomers of the formula

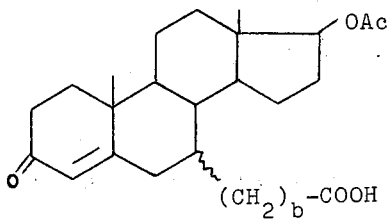 XV reacting the latter with a saponification agent to obtain the corresponding 17β-hydroxy compound of formula I and the 7α-and 7β-isomers may be separated by known methods.

Examples of suitable acids are alkanoic acids such as formic acid, acetic acid, propionic acid, butyric acid, isobutyric acid, valeric acid, isovaleric acid, trimethyl acetic acid, caproic acid, β-trimethylpropionic acid, heptanoic acid, caprylic acid, pelargonic acid, capric acid, undecylic acid, lauric acid, myristic acid, palmitic acid and stearic acid; alkenoic acids such as undecylenic acid and oleic acid; cycloalkyl carboxylic acids such as cyclopentyl carboxylic acid, cyclopropyl carboxylic acid, cyclobutyl carboxylic acid and cyclohexyl carboxylic acid; cycloalkyl alkanoic acids such as cyclopentyl acetic acid, cyclohexyl acetic acid, cyclopentyl propionic acid and cyclohexyl propionic acid; arylalkanoic acids such as phenylacetic acid and phenylpropionic acid; aryl carboxylic acids such as benzoic acid and 2,4-dinitrobenzoic acid; phenoxy alkanoic acids such as phenoxyacetic acid, p-chlorophenoxy acetic acid, 2,4-dichlorophenoxy acetic acid, 4-tert.-butylphenoxy acetic acid, 3-phenoxy propionic acid and 4-phenoxy butyric acid; heterocyclic carboxylic acids such as furane-2-carboxylic acid, 5-tert.-butylfurane-2-carboxylic acid, 5-bromofurane-2-carboxylic acid and nicotinic acids; β-ketoalkanoic acids such as acetylacetic acid, propionylacetic acid and butrylacetic acid; amino acids such as diethylaminoacetic acid and aspartic acid.

The organo magnesium halide is preferably the chlorine or bromide and M is preferably benzyl or tetrahydropyranyl. The acid agent is preferably hydrochloric acid, sulfuric acid, acetic acid, citric acid or p-toluene-sulfonic acid and the reaction is effected in at least one solvent such as lower alkanols like methanol, ethanol or isopropanol, a ketone such as acetone or a hydrocarbon such as benzene or toluene.

The oxidation agent is preferably chormic anhydride, silver carbonate, silver silicate or lead tetraacetate. The saponification agent is preferably an alkaline base such as alkali metal hydroxide like sodium or potassium hydroxide; alkali metal amides such as sodium amide; alkali metal alcoholates like potassium tert.-butylate; and alkali metal acetylides like lithium acetylide in ethylenediamine. The separation of the 7α- and 7β-isomers may be effected by chromatography.

The starting compounds of formula XI are generally known and may be prepared by the process described by Meystre et al [Experientia, (1946), p.408].

The process of the invention for the preparation of compounds of formula I wherein Y is hydrogen and X is =N—O—(CH₂)$_c$—COOH comprises reacting a compound of the formula

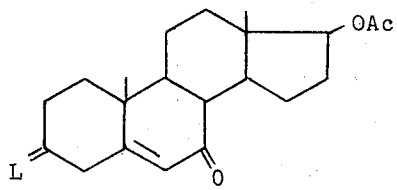

XVI wherein Ac has the above definition and L is a ketal with a compound of the formula

H₂N—O—(CH₂)$_c$—COOH  XVII to obtain a compound of the formula

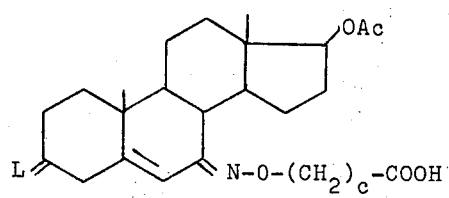

XVIII reacting the latter with a saponification agent to obtain a compound of the formula

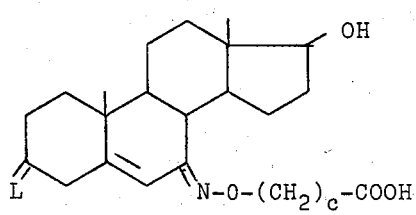

XIX and subjecting the latter to acid hydrolysis to obtain the desired compound of formula I.

L is preferably a cyclic alkyleneketal of 2 to 4 carbon atoms such as ethyleneketal or propyleneketal or a dialkylketal such as dimethylketal or diethylketal. The compound of formula XVII is preferably used in the form of its acid addition salts such as the hydrochloride. The acid agent is preferably hydrochloric acid, acetic acid or perchloric acid and most preferably perchloric acid in chloroform. The starting materials of formula XVI are generally known and may be prepared by the process of U.S. Pat. No. 2,934,545.

The novel process of the inention for the preparation of antigens comprises reacting a compound of formula I with an alkyl orthoformate to obtain a mixed acid anhydride and reacting the latter with beef serum albumin to form the antigen. The alkyl orthoformate is preferably isobutyl orthoformate.

The antibodies which can be prepared from these antigens may be prepared by classical methods such as described by Erlanger /J. Biol. Chem., Vol. 228, p. 713/. These antibodies are specific to testosterone and this specificity is used in the classical methods, notably by dialysis to equilibrium. This specificity makes these antibodies useful as dosage agents of testosterone and are of interest in the dosage in therapy.

In the following examples there are described several preferred embodiments to illustrate the invention. However, it is to be understood that the invention is not intended to be limited to the specific embodiments

EXAMPLE 1

11α-hemisuccinoyloxy-Δ⁴-androstene-17β-ol-3-one 0.234 g of sodium borohydride were added to a solution of 1.266 g of 11α-hemisuccinoyloxy-Δ⁴-androstene-3,17-dione [prepared by the method of Wataru et al, Chem. Pharm. Bull., Vol. 14 (2) (1966), p. 174] in 215 ml of methanol and the mixture was stirred at 0°C for 1½ hours. 2 ml of acetic acid were added and the mixture was extracted with methylene chloride and the organic extracts was washed with water, dried and concentrated to dryness to obtain 1.396 g of an amphorus product. The product was chromatographed over silica gel and was eluted with a 10-90-2 mixture of cyclohexane-ethyl acetate-acetic acid to obtain 0.595 g of 11α-hemisuccinoyloxy-Δ⁴-androstene-17β-ol-3-one melting at 209°–210°C.

EXAMPLE 2

11β-hemisuccinoyloxy-Δ⁴-androstene-17β-ol-3-one

STEP A: 11β-hemisuccinoyloxy-Δ⁴-androstene-3,17-dione

A mixture of 2 g of Δ⁴-androstene-11β-ol-3,17-dione, 6.4 g of succinic acid anhydride, 2 g of 4-dimethylaminopyridine and 10 ml of pyridine was heated at 100°C for 24 hours and was then cooled to room temperature. Water was added to the mixture which was then extracted with methylene chloride. The organic extracts were washed with water and concentrated to dryness. The residue was chromatographed over silica gel and was eluted with a 5-95-1 mixture of cyclohexane-ethylacetate-acetic acid to obtain 1.368 g of 11β-hemisuccinoyloxy-Δ⁴-androstene-3,17-dione.

STEP B: 11β-hemisuccinoyloxy-Δ⁴-androstene-17β-ol-3-one 0.191 g of sodium borohydride were added to a solution of 1.039 g of the produt of Step A in 150 ml of methanol and the mixture was heated at 100°C for 23 hours. After cooling to room temperature, water was added to the mixture which was then extracted with methylene chloride. The organic extracts were washed with water, dried and concentrated to dryness. The residue was chromatographed over silica gel and was eluted with a 5-95-1 mixture of cyclohexane-ethyl acetate-acetic acid to obtain 0.4 g of 11β-hemisuccinoyloxy-Δ⁴-androstene-17β-ol-3-one melting at 218°C.

EXAMPLE 3

11α-hemiterephthaloyloxy-Δ⁴-androstene-17β-ol-3-one

STEP A: 11α-(p-methoxycarbonylbenzoyloxy)-Δ⁴-androstene-3,17-dione

A mixture of 0.71 g of Δ⁴-androstene-11α-ol-3,17-dione, 1.60 g of p-methoxycarbonyl benzoic acid anhydride and 2.8 ml of pyridine was stirred at 100°C for 3½ hours and the mixture was extracted with methylene chloride. The organic extracts were washed with water and concentrated to dryness. The residue was chromatographed over silica gel and was eluted with a 60-40-2 mixture of cyclohexane-ethyl acetate-acetic acid to obtain 0.89 g of 11α-(p-methoxycarbonylbenzoyloxy)-Δ⁴-androstene-3,17-dione melting at 168°C and then 176°C and had a specific rotation $[\alpha]_D^{20} = +20° \pm 2.5°$ (c = 0.45% in chloroform).

STEP B: 11α-(p-methoxycarbonylbenzoyloxy)-Δ⁴-androstene-17β-ol-3-one

A mixture of 2.4 g of the product of Step A in 12 ml of dioxane, 3 ml of ethyl orthoformate and 0.096 g of p-toluene sulfonic acid was stirred at 28°C for 35 minutes under an inert gas and then 0.6 ml of triethylamine were added thereto followed by 8 ml of water. The mixture was extracted with methylene chloride and the organic extracts were washed with water and concentrated to dryness to obtain 2.55 g of 3-ethoxy-11α-(p-methoxycarbonylbenzoyloxy)-Δ³,⁵-androstadiene-17-one. The said product was dissolved in 25.5 ml of tetrahydrofuran and 25.5 ml of methanol and then a solution of 0.812 g of sodium borohydride in 4.25 ml of water was progressively added thereto at 0°C. The mixture was stirred for 45 minutes at 0°C and then 350 ml of water were added. The mixture was filtered to obtain 2.56 g of 3-ethoxy-11α-(p-methoxycarbonylbenzoyloxy)-Δ³,⁵-androstadiene-17β-ol and the said product was dissolved in 9.1 ml of ethanol. 0.9 ml of N hydrochloric acid were added to the solution and after stirring the mixture for 30 minutes, 50 ml of water were added thereto. The mixture was filtered and the recovered precipitate was crystallized from a methylene chloride-petroleum ether (bp = 60°–80°C) mixture to obtain 2.221 g of 11α-(p-methoxycarbonylbenzoyloxy)-Δ⁴-androstene-17β-ol-3-one melting at 221°C.

STEP C: 11α-hemiterephthaloyloxy-Δ⁴-androstene-17β-ol-3-one 6.5 ml of N sodium hydroxide solution were added dropwise to a solution of 2.16 g of the product of Step B in 216 ml of ethanol and the mixture was stirred at 40°C for 3 hours. After cooling the mixture to 0°C, a solution of N hydrochloric acid was added thereto to adjust the pH to 2 and then 1800 ml of water were added progressively over about 1 hour. The mixture was filtered and the recovered precipitate was chromatographed over silica gel and a 3-7-0.1 mixture of cyclohexane-ethyl acetate-acetic acid was eluent to obtain 0.726 g of 11α-hemiterephthaloyloxy-Δ⁴-androstene-17β-ol-3-one melting at 278°C with decomposition and having a specific rotation of $[\alpha]_D^{20} = +2.5° \pm 2°$ (c = 0.6% in ethanol).

EXAMPLE 4

11β-hemiterephthaloyloxy-Δ⁴-androstene-17β-ol-3-one

STEP A: 11β-(p-methoxycarbonylbenzoyloxy)-Δ⁴-androstene-3,17-dione

A mixture of 63 g of Δ⁴-androstene-11β-ol-3,17-dione, 70 ml of triethylamine, 126 g of p-methoxycarbonyl benzoic acid anhydride, 6.3 g of p-dimethylaminopyridine and 2 liters of methylene chloride was refluxed for 4 hours and then after the addition of 3 g of p-dimethylaminopyridine, for another 24 hours. The reaction mixture was poured into 3 liters of an aqueous saturated sodium bicarbonate solution and the mixture was extracted with methylene chloride. The organic extracts were washed with water and concentrated to dryness under reduced pressure. The residue was chromatographed over silica gel and was eluted with an 8-2 mixture of benzeneethyl acetate to obtain 58 g of 11β-(p-methoxycarbonylbenzoyloxy)-Δ⁴-androstene-3,17-dione.

STEP B: 11β-(hemiterephthaloyloxy)-Δ⁴-androstene-17β-ol-3-one

A mixture of 2.28 g of the product of Step A, 12 ml of dioxane, 1.7 ml of ethyl orthoformate and 0.115 g of p-toluene sulfonic acid was held at 18°C for 30 minutes under an inert gas and then 0.25 ml of triethylamine were added. Water was then added to cause a precipitation and the mixture was filtered to obtain the precipitate of 3-ethoxy-11β-(p-methoxycarbonylbenzoyloxy)-Δ³,⁵-androstadiene-17-one.

The said product was suspended in 20 ml of methanol and 10 ml of tetrahydrofuran and 1 g of sodium borohydride was added thereto at 5°C. The mixture was stirred for 30 minutes and then 10 ml of N sodium hydroxide solution were added. The mixture stood at room temperature for 2 hours and was then acidified to a pH of 5 by addition of 2N hydrochloric acid solution. The mixture was filtered and the recovered precipitate of 3-ethoxy-11β-hemiterephthaloyloxyΔ³,⁵-androstadiene-17β-ol was suspended in 15 ml of ethanol and 2 ml of 2N hydrochloric acid. The suspension was heated to 50°C until dissolution occured and the solution was cooled to room temperature and was filtered. The recovered precipitate was crystallized from ethanol to obtain 1.330 g of 11β-hemiterephthaloyloxy-Δ⁴-androstene-17β-ol-3-one melting at 283°C and having a specific rotation of $[\alpha]_D^{20} = +187° \pm 3.5°$ (c = 0.55% in chloroform).

EXAMPLE 5

7α-and 7β-(ω-carboxydecyl)-Δ⁴-androstene-17β-ol-3-one

A solution of 65 g of 11-tetrahydropyranyloxy-1-bromo-decane in 200 ml of tetrahydrofuran was progressively added to a mixture of 5 g of magnesium and 40 ml of tetrahydrofuran while keeping the temperature at about 45°C. 0.6 g of cuprous chloride were added at −20°C to the resulting solution and then a solution of 30 g of 17β-acetoxy-Δ$^{4,6}$-androstadiene-3-one in 200 ml of tetrahydrofuran was progressively added at −20°C. The mixture was held at −20°C for 30 minutes after the last addition and then 300 ml of an aqueous ammonium chloride solution were added thereto. The reaction mixture was poured into water and was extracted with ethyl acetate and was evaporated to dryness. The residue was chromatographed over silica and was eluted with a 9-1 benzene-ethyl acetate mixture to obtain a first fraction of 11.5 g of 7ξ-(ω-tetrahydropyranyloxyundecyl)-17β-acetoxyΔ$^5$-androstene-3-one and a second fraction of 25 g of 7ξ-(ω-tetrahydropyranyloxyundecyl)17β-acetoxy-Δ$^4$-androstene-3-one.

The first fraction of 11.5 g was dissolved in 60 ml of methanol and 5.5 ml of N hydrochloric acid and after standing at room temperature for 2½ hours, the mixture stood at 45°C for one hour. The reaction mixture was poured into water and was extracted with methylene chloride. The organic extracts were evaporated to dryness and the residue was chromatographed over silica gel and eluted with a 70-30 benzene-ethyl acetate mixture to obtain 6.8 g of 7ξ-(ω-hydroxyundecyl)-17β-acetoxy-Δ$^4$-androstene-3-one with an Rf of 0.19. Treatment of the 25 g of the second fraction in the same way resulted in the same product.

6.8 g of the said product were dissolved in 150 ml of acetone and 9 ml of a mixture of 270 g of $CrO_3$, 230 ml of sulfuric acid and sufficient water to obtain a total of 1 liter were added dropwise at 0° to 5°C. The mixture was then stirred at 0° to 5°C for 1 hour and 5 ml of methanol were added thereto. The mixture was filtered and the filtrate was concentrated to 30 ml by evaporation under reduced pressure. The solution was diluted with water and was extracted with methylene chloride. The organic extracts were evaporated to dryness to obtain 7ξ-(ω-carboxydecyl)-17β-acetoxy-Δ$^4$-androstene-3-one which showed by thin layer chromatography an Rf = 0.28 (silica gel support - 70-30-2 eluant of benzene-ethylacetateacetic acid).

5.8 g of the said product were dissolved in 60 ml of ethanol and 30 ml of 2N sodium hydroxide solution were added thereto. The mixture was stirred for 30 minutes at room temperature and was made acidic by addition of 2N hydrochloric acid. The reaction mixture was poured into water and was extracted with methylene chloride. The organic extracts were evaporated to dryness and the residue was chromatographed over silica gel and was eluted with a 70-30-2 mixture of benzene-ethyl acetate acid to separately obtain 7α-(ω-carboxydecyl)-Δ$^4$-androstene-17β-ol-3-one melting at 133°C and having a specific rotation of $[\alpha]_D^{20} = +47°$ ± 2° (c = 0.5% in chloroform) and 7β-(ω-carboxydecyl)-Δ$^4$-androstene-17β-ol-3-one melting at 98°C and having a specific rotation of $[\alpha]_D^{20} = +58.5° ± 4.5°$ (c = 0.5% in chloroform).

EXAMPLE 6

7-carboxymethoxyimino-Δ$^4$-androstene-17β-ol-3-one

STEP A: 7-carboxymethoxyimino-3,3-ethylenedioxy-Δ$^5$-androstene-17β-ol

A mixture of 5 g of 3,3-ethylenedioxy-17-acetoxy-Δ$^5$-androstene-7-one, 250 ml of ethanol, 5 g of 0-carboxymethylhydroxylamine hydrochloride and 44 ml of N sodium hydroxide solution was refluxed for 4 hours, and after the addition of 5 ml of a concentrated sodium hydroxide solution, reflux was continued for 30 minutes The mixture was cooled to room temperature and 50 ml of 2N hydrochloric acid and 400 ml of water were added thereto. The mixture was filtered and the recovered precipitate was crystallized from a mixture of 50 ml of ethyl acetate and 20 ml of methanol to obtain 2.24 g of 3,3-ethylenedioxy-7-carboxymethoxyimino-Δ$^5$-androstene-17β-ol which when crystallized from ethanol melted at 216°C.

STEP B: 7-carboxymethoxyimino-Δ$^4$-androstene-17β-ol-3-one

A mixture of 1 g of 3,3-ethylenedioxy-7-carboxymethoxyimino-Δ$^5$-androstene-17β-ol, 10 ml of chloroform and 10 ml of a 70% perchloric acid aqueous solution was stirred for 2 minutes at 20°–25°C and was then poured into 90 ml of an aqueous saturated sodium bicarbonate solution. The chloroform was evaporated at 25°C under reduced pressure and the mixture was filterd to obtain 0.794 g of 7-carboxymethoxyimino-Δ$^4$-androstene-17β-ol-3-one melting at 162°C. The UV spectrum showed that the product was partially in the enolic form (Δ$^{3,5}$-3-OH was about 50%).

EXAMPLE 7

PREPARATION OF ANTIGENS WITH BOVINE SERUM ALBUMIN

The conjugation of 7(ω-carboxydecyl)-Δ$^4$-androstene -17β-ol-3-one and bovine serum albumin (BSA) was prepared by the classical method of first forming a mixed anhydride of 7-(ω-carboxydecyl)-Δ$^4$-androstene-17β-ol-3-one of the formula

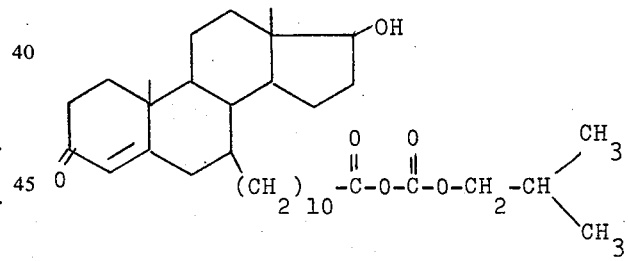

which is then condensed in a second step with BSA as follows:

0.132 ml of isobutyl chlorocarbonate were added to a mixture of 473 mg of 7β-(ω-carboxydecyl)-Δ$^4$-androstene-17β-ol-3-one, 10 ml of dioxane and 0.246 ml of tri-n-butylamine and the mixture was stirred for 20 minutes at 12°C to form the desired mixed anhydride. 36 ml of dioxane were added to a solution of 1.38 g of BSA in 36 ml of ice water to obtain a whitish suspension which totally redissolved after the addition of 1.38 ml of N sodium hydroxide solution. The mixed anhydride solution was added to the resulting solution and the mixture was stirred for one hour at 0° to 4°C. Then, 0.655 ml of N sodium hydroxide solution was added thereto and the mixture was stirred for 3 hours at 0° to 4°C at a pH of 9.2. The reaction mixture was subjected to dialysis while passing with a micropump 15 liters of water in 74 hours at 2° to 5°C. The pH was adjusted to 4.5 by addition of 2N hydrochloric acid and the resulting colloidal antigen suspension was held at −20°C for 4 hours after which the temperature was returned to room temperature. The precipitate formed was recovered by decantion and was dissolved in 120 ml of an aqueous 1% sodium bicarbonate solution 2N hydrochloric acid was added to the mixture to adjust the pH to 6.5 and the solution was subjected to dialysis as before for 20 hours at 0° to 4°C. The desired product was isolated by lyophilization and was purified by dissolving 1.3 g in 100 ml of ice water and the solution was extracted 3 times with 20 ml of iced chloroform to remove excess free acid. The aqueous phase was then subjected to lyophilization to obtain 1.060 g of a white powder which was the desired product. The UV spectrum showed that the product contain 18% by weight of the acid steroid (16.5% bound acid and 1.5% free acid). The circular dichroism curve showed that the product contained 22.5% by weight of the acid steroid. Microanalysis showed 13.2–13.3% nitrogen and 5.6% water after drying at 80°C and 4.6% of ash.

Various modifications of the products and methods of the invention may be made without departing fron the spirit or scope thereof and it is to be understood that the invention is to be limited only as defined in the appended claims.

We claim:

1. A haptene of the formula

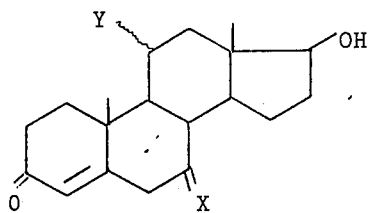

wherein X is

when Y is

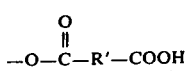

in the α- or β-position and R'' is selected from the group of p-phenylene and —(CH$_2$)$_a$— and $a$ is a whole number from 1 to 18 with the proviso that $a$ is other than 2 and when Y is hydrogen, X is selected from the group consisting of

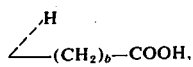

and

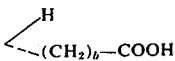

and =N—O—(CH$_2$)$_c$—COOH, $b$ is a whole number from 1 to 18 and $c$ is a whole number from 1 to 12.

2. A compound of claim 1 wherein X is

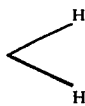

and Y is

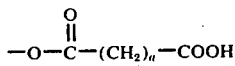

in the α-or β-position with the proviso that $a$ is other than 2 when Y is in the α-position.

3. A compound of claim 1 wherein X is

and Y is

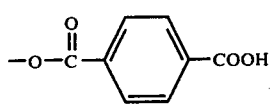

in the α- or β-position.

4. A compound of claim 1 wherein Y is hydrogen and X is

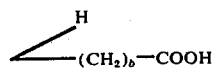

or

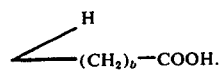

5. A compound of claim 1 wherein Y is hydrogen and X is =N—O—(CH$_2$)$_c$—COOH.

6. A compound of claim 1 which is 11α-hemiterephthaloyloxy-Δ$^4$-androstene-17β-ol-3-one, 7. A compound of claim 1 which is 11β-hemiterephthaloyloxy-Δ$^4$-androstene-17β-ol-3-one.

8. A compound of claim 1 which is 7α-(ω-carboxydecyl)-Δ$^4$-androstene-17β-ol-3-one.

9. A compound of claim 1 which is 7β-(ω-carboxydecyl)-Δ$^4$-androstene-17β-ol-3-one.

10. A compound of claim 1 which is 7-carboxymethoxyimino-Δ$^4$-androstene-17β-ol-3-one.

* * * * *

UNITED STATES PATENT OFFICE
CERTIFICATE OF CORRECTION

Patent No. 3,975,413          Dated  Aug. 17, 1976

Inventor(s)  ANDRE PIERDET and DANIEL COUSSEDIERE

It is certified that error appears in the above-identified patent and that said Letters Patent are hereby corrected as shown below:

| Col. | Line |  |
|---|---|---|
| 1 | 50 | " $\diagdown \mathrm{H} \atop \diagup \mathrm{H}$ " should be -- $\diagdown {\mathrm{H} \atop \mathrm{H}}$ -- |
| 2 | 1 | " $\diagup \mathrm{H} \atop \diagdown (CH_2)_b-COOH$ , $\diagdown \mathrm{H} \atop (CH_2)_b-COOH$ " should be -- $\diagup \mathrm{H} \atop \diagdown (CH_2)_b-COOH$, $\diagdown \mathrm{H} \atop (CH_2)_b-COOH$ -- |
| 2 | 20 | " $\diagup \mathrm{H} \atop \diagdown \mathrm{H}$ " should be -- $\diagdown {\mathrm{H} \atop \mathrm{H}}$ -- |
| 2 | 34 | "62position" should be --β-position-- |
| 2 | 45 | " $\diagdown \mathrm{H} \atop (CH_2)_b-COOH$ " should be -- $\diagdown \mathrm{H} \atop (CH_2)_b-COOH$ -- |
| 2 | 55 | " $\diagdown \mathrm{H} \atop (CH_2)_b-COOH$ " should be -- $\diagup \mathrm{H} \atop \diagdown (CH_2)_b-COOH$ -- |

UNITED STATES PATENT OFFICE
CERTIFICATE OF CORRECTION

Patent No. 3,975,413   Dated Aug. 17, 1976

Inventor(s) ANDRE PIERDET and DANIEL COUSSEDIERE

It is certified that error appears in the above-identified patent and that said Letters Patent are hereby corrected as shown below:

| Col. | Line | |
|---|---|---|
| 3 | 1 | "$\prec^H_H$" should be --$\prec^H_H$-- |
| 4 | 15 | "   "   "   "   "   "   " |
| 6 | 35 | "$\prec^H_{(CH_2)_b-COOH}$" should be --$\prec^H_{(CH_2)_b-COOH}$-- |
| 6 | 45 | "$\prec^H_{(CH_2)_b-COOH}$" should be --$\prec^H_{(CH_2)_b-COOH}$-- |
| 12 | 32 | "benzeneethyl" should be --benzene-ethyl-- |
| 13 | 68 | "17 -" should be --17β- -- |

UNITED STATES PATENT OFFICE
CERTIFICATE OF CORRECTION

Page 3 of 3

Patent No. 3,975,413      Dated Aug. 17, 1976

Inventor(s) ANDRE PIERDET and DANIEL COUSSEDIERE

It is certified that error appears in the above-identified patent and that said Letters Patent are hereby corrected as shown below:

| Col. | Line | | |
|---|---|---|---|
| | Claim 1 | | |
| 15 | 50 | "R" " | should be --R'-- |
| | Claim 2 | | |
| 16 | 8 | "$\diagup^H_{\diagdown H}$" | should be --$\diagup^H_{\diagdown H}$-- |
| | Claim 3 | | |
| 16 | 25 | " " " " " " " " " " " " " | |
| | Claim 4 | | |
| 16 | 44 | " " " " " " " " " " " " " | |
| | Claim 4 | | |
| 16 | 50 | " " " " " " " " " " " " " | |

Signed and Sealed this

Twenty-fifth Day of January 1977

[SEAL]

Attest:

RUTH C. MASON  
Attesting Officer

C. MARSHALL DANN  
Commissioner of Patents and Trademarks